(12) United States Patent
Hino

(10) Patent No.: US 12,144,673 B2
(45) Date of Patent: Nov. 19, 2024

(54) FETAL GROWTH RESTRICTION INSPECTION APPARATUS

(71) Applicant: Katsuhiko Hino, Sendai (JP)

(72) Inventor: Katsuhiko Hino, Sendai (JP)

( * ) Notice: Subject to any disclaimer, the term of this patent is extended or adjusted under 35 U.S.C. 154(b) by 333 days.

(21) Appl. No.: 17/774,960

(22) PCT Filed: Nov. 7, 2019

(86) PCT No.: PCT/JP2019/043638
§ 371 (c)(1),
(2) Date: May 6, 2022

(87) PCT Pub. No.: WO2021/090434
PCT Pub. Date: May 14, 2021

(65) Prior Publication Data
US 2022/0386986 A1 Dec. 8, 2022

(51) Int. Cl.
*A61B 8/06* (2006.01)
*A61B 8/08* (2006.01)

(52) U.S. Cl.
CPC ............... *A61B 8/06* (2013.01); *A61B 8/488* (2013.01)

(58) Field of Classification Search
CPC ......... A61B 10/00; A61B 8/06; A61B 8/0866; A61B 8/468; A61B 8/488; A61B 8/5207
See application file for complete search history.

(56) References Cited

U.S. PATENT DOCUMENTS

2019/0099153 A1* 4/2019 Weinberg ................ A61B 8/06

OTHER PUBLICATIONS

R.L.A. Erskine and J.W.K. Ritchie, "Umbilical artery blood flow characteristics in normal and growth-retarded fetuses," Jun. 1985, British Journal of Obstetrics and Gynaecology, vol. 92, pp. 605-610 (Year: 1985).*
E. Ferrazzi et al., "Uterine artery blood flow volume in pregnant women with an abnormal pulsatility index of the uterine arteries delivering normal or intrauterine growth restricted newborns," Jul. 2011, Placenta, vol. 32 Issue 7, pp. 487-492 (Year: 2011).*
International Search Report w/ English translation dated Dec. 17, 2019, issued in counterpart International Application No. PCT/JP2019/043638.
Written Opinion of the International Searching Authority dated Dec. 17, 2019, issued in the counterpart International Application No. PCT/JP2019/043638.

* cited by examiner

*Primary Examiner* — Joseph M Santos Rodriguez
*Assistant Examiner* — Maria Christina Talty
(74) *Attorney, Agent, or Firm* — Muncy, Geissler, Olds & Lowe, P.C.

(57) ABSTRACT

An inspection apparatus includes a measurement apparatus that measures an inner diameter and a blood flow velocity in an artery from a fetus to a placenta of a pregnant woman, a calculation apparatus that calculates a Reynolds number based on the inner diameter and the blood flow velocity in the artery measured by the measurement apparatus, and a determination apparatus that determines, for a pregnant woman who is 20 weeks or more pregnant, that the fetus may be developing FGR in a case that the Reynolds number is less than a first threshold value.

13 Claims, 3 Drawing Sheets

FETAL GROWTH RESTRICTION INSPECTION APPARATUS

TECHNICAL FIELD

The present invention relates to an inspection apparatus for assisting in the diagnosis of fetal growth.

BACKGROUND OF THE INVENTION

One of the fetal assessments in perinatal care is an assessment pertaining to fetal growth restrictions (FGR). FGRs are defined as conditions in which the fetal estimated body weight is less than or equal to −1.5 standard deviations (SD) of the fetal growth standard by gestational age. Once diagnosed with FGR, appropriate treatment can be given early, potentially leading to a normal delivery.

In order to obtain the estimated fetal weight, the estimated fetal weight (EFW) formula, which is a theoretical formula based on a fetal model in which the fetus is divided into a head and a trunk, is often used. An example of the EFW formula is illustrated below.

$$EFW = 1.07 \times BPD^3 + 0.30 \times AC^2 \times FL \qquad (1)$$

Here, BPD represents the fetus' head size (biparietal diameter), AC represents the length of the abdominal circumference, and FL represents the femoral length (femur length).

Measurements are made using ultrasonic tomography to determine the dimensions of the fetus in the mother's body. The ultrasonic tomography method has the advantage that ultrasonic waves that are non-invasive to the mother and the fetus can be used, but some measurement error may occur depending on the posture of the fetus at the time of measurement. In addition, in order to compare the estimated fetal weight obtained by the EFW formula with the weight reference value, it is necessary to reference the pregnancy week number, but there may be deviation in the pregnancy week number due to individual differences of the mother. Accordingly, it is difficult to diagnose whether or not FGR is present according to the EFW formula using a single test, and generally, the diagnosis is made through a plurality of tests.

On the other hand, Non-Patent Document 1 discloses a technique for diagnosing a fetus by measuring the blood flow velocity of the umbilical cord artery by an ultrasonic pulse Doppler method. Specifically, the systolic maximum blood flow velocity S, the diastolic end-stage blood flow velocity D, and the average blood flow velocity Mean are obtained by the ultrasonic pulse Doppler method, and the Resistance Index (RI) value and the Pulsatility Index (PI) value are obtained from these values as follows.

$$RI = (S-D)/S \qquad (2)$$

$$PI = (S-D)/\text{Mean} \qquad (3)$$

CITATION LIST

Non-Patent Documents

[Non-Patent Document 1] Kudo Yoshiki," Obstetrical and Gynecological Examination; 15. (Assessment of Fetal Umbilical Blood Flow)," Journal of the Japanese Society of Obstetrics and Gynecology, Vol. 59, No. 6, June 2007

SUMMARY OF INVENTION

Technical Problem

As described in Non-Patent Document 1, both the RI value and the PI value tend to decrease as the pregnancy week number increases after 20 weeks of pregnancy. The reason is explained that in normal pregnancies, vascular resistance decreases and fetal placental circulation is maintained as the pregnancy progresses. On the other hand, it is explained that FGR impairs fetal placental circulation and both the RI and PI values become higher than normal values.

However, increases in the RI value and the PI value may occur in cases other than FGR, and there are cases in which the RI value and the PI value do not increase even when FGR is present. For this reason, tests using RI or PI values are considered to not be suitable for screenings for the purpose of detecting FGR, and the situation is such that the estimated fetal weight measured by ultrasonic tomography is used exclusively for the diagnosis of FGR. The present inventor has conducted extensive research and found a technique capable of easily diagnosing the growth state of a fetus based on new findings.

The present invention has been made in view of the problems of the prior art, and has an object of providing an inspection apparatus capable of easily and accurately determining the growth state of a fetus.

Means for Solving the Problems

The inspection apparatus according to the present invention includes a measurement apparatus that measures an inner diameter and a blood flow velocity of an artery extending from a fetus to a placenta of a pregnant woman; a calculation apparatus that calculates a Reynolds number based on the inner diameter and the blood flow velocity of the artery measured by the measurement apparatus; an input apparatus that inputs a pregnancy week number; and a determination apparatus that determines, based on the pregnancy week number and the Reynolds number, whether or not the fetus is developing FGR.

Effect of the Invention

According to the present invention, it is possible to provide an inspection apparatus capable of easily and accurately determining the growth state of a fetus.

DESCRIPTION OF EMBODIMENT(S)

Figure 1:
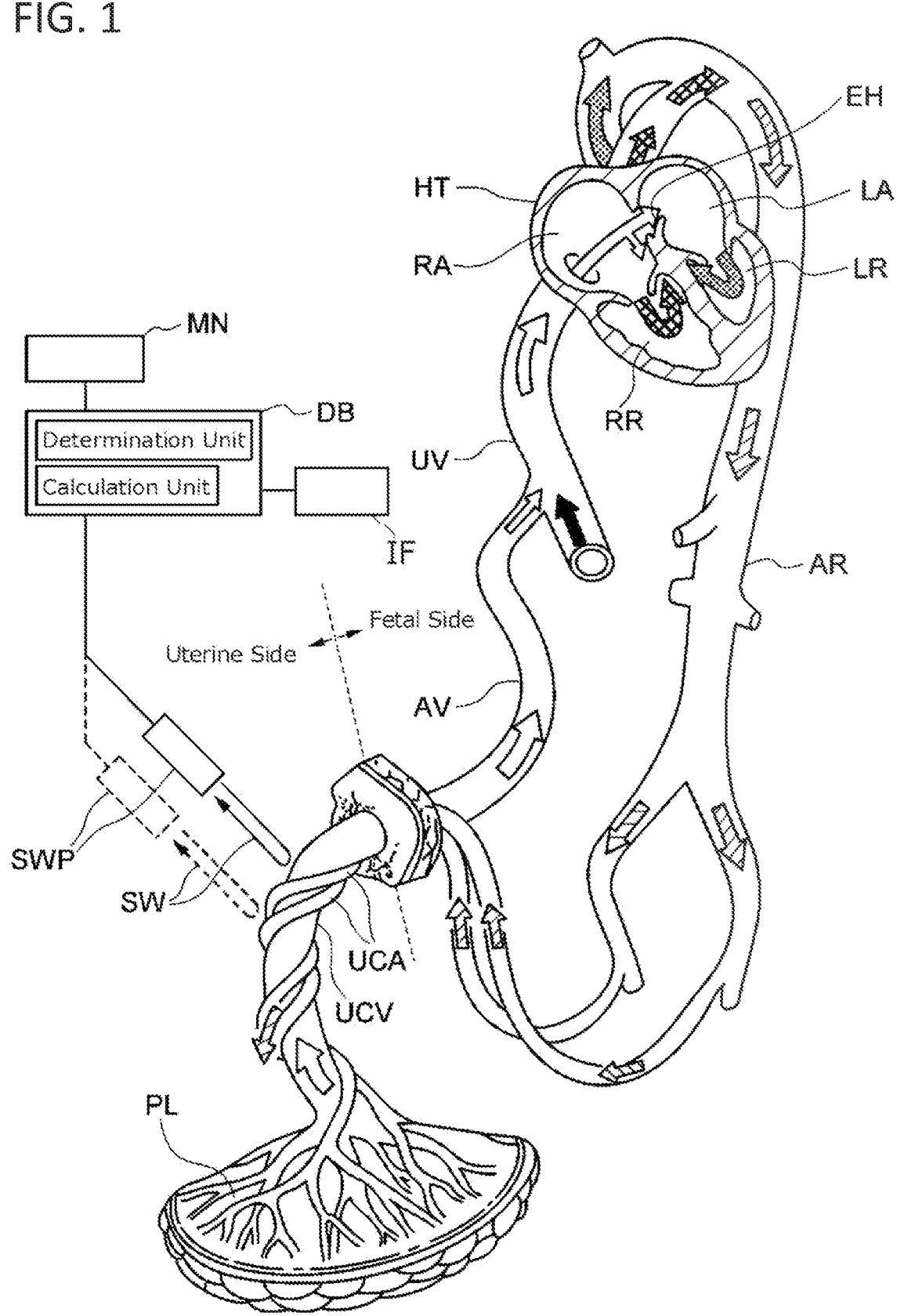
FIG. 1 is a diagram illustrating an inspection apparatus according to the present embodiments together with a feto-placental circulatory system.

The present embodiments will be described with reference to the drawings. FIG. 1 is a diagram illustrating an inspection apparatus according to the present embodiments together with a fetoplacental circulatory system. Fetal oxygenation depends on the placenta, and the presence of a blood flow shunt is required for oxygen to be effectively utilized. In FIG. 1, the fetal blood oxygenated by the placenta PL enters the fetus via the umbilical cord vein UCV, and further enters the right atrium RA of the fetal heart HT from the ductus venosal AV via the inferior vena cava UV. The fetal blood then flows into the left atrium LA via the foramen ovale EH, passes through the left ventricle LR, and is carried to the brain, upper body, or lower body of the fetus through an aorta (not illustrated in the figure).

On the other hand, fetal blood with low oxygen content enters the right atrium RA of the heart HT from the vena cava, passes through the aorta AR via the right ventricle RR, is discharged out of the fetus via the umbilical cord artery UCA, and returns to the placenta PL.

The placenta PL is an organ in which the villus, which is a fetal component, is floating in an intervillous space, which is the maternal component. Here, not only does maternal-fetal material exchange occur, but many other substances, including hormones and enzymes, are produced. The placenta PL also serves as an immune barrier. That is, the fetal blood flowing through the umbilical cord artery UCA can be interpreted as having a predetermined energy consumption in the placenta PL.

The inspection apparatus according to the present embodiment includes an ultrasonic probe SWP, an apparatus main body DB connected to the ultrasonic probe SWP, an input device IF such as a keyboard for inputting the pregnancy week number, and a monitor MN for displaying a result. A personal computer or the like can be used as the apparatus main body DB.

The ultrasonic probe SWP has a plurality of piezoelectric elements, and this plurality of piezoelectric elements generate an ultrasonic wave SW based on a drive signal supplied from a transceiver unit of the apparatus main body DB. In addition, the plurality of piezoelectric elements included in the ultrasonic probe SWP receive reflected waves from the vessel walls of the umbilical cord vein UCV and the umbilical cord artery UCA as well as the fetal blood flowing in the blood vessels, and convert the reflected waves into electrical signals. These electric signals are input to the apparatus main body DB, and after being calculated by a calculation unit inside the apparatus main body DB as will be described later, are determined by a determination unit. The determination result is displayed on the monitor MN. The ultrasonic probe constitutes a measurement apparatus, the calculation unit constitutes a calculation apparatus, and the determination unit constitutes a determination apparatus.

When the ultrasonic probe SWP is arranged to face the umbilical cord vein UCV or the umbilical cord artery UCA from the outside of the mother's body and the pulsed ultrasonic wave SW is oscillated, the emitted ultrasonic wave SW is reflected by the vessel walls of the umbilical cord vein UCV or the umbilical cord artery UCA and the fetal blood flow moving in the blood vessels, and is received as a reflected wave signal by the plurality of piezoelectric elements included in the ultrasonic probe SWP.

The inner diameter of the blood vessels can be obtained by utilizing the fact that the ultrasonic waves have a property of reflecting at portions having a difference in acoustic impedance. In addition, by utilizing the fact that the reflected wave signal is subjected to a frequency deviation depending on the velocity component of the fetal blood flow with respect to the ultrasonic wave transmission direction due to the Doppler effect, and by calculating this frequency deviation using the calculation unit in the apparatus main body DB, the blood flow velocity can be obtained. As such an ultrasonic probe SWP, for example, those described in Japanese Unexamined Patent Application Publication No. 2010-214013 and Japanese Unexamined Patent Application Publication No. 2014-207979 can be used, but the present invention is not limited thereto.

The present inventor considered whether the growth state of the fetus could be diagnosed from a completely different perspective from the conventional medical view. In perinatal management, observation of the blood flow in the umbilical cord artery is already performed. However, blood flow in the umbilical cord artery has not been analyzed from a hydrodynamic point of view. As a result of extensive research, the present inventor has found that there is a close relationship between the Reynolds number of the blood flow in the umbilical cord artery and the growth state of the fetus.

The Reynolds number is a dimensionless quantity defined by the ratio of inertial force to viscous force (inertial force/viscous force) in fluid mechanics, and it can be determined whether a flow is a laminar flow or a turbulent flow according to the magnitude of the Reynolds number. Laminar flow occurs at low Reynolds numbers where viscous forces are dominant, and is characterized by smooth and stable flow. On the other hand, turbulent flow occurs at high Reynolds numbers where inertial forces are dominant, and is characterized by disordered vortices and unstable flows.

In a general flow in a mechanical pipe, since laminar flow is preferred for efficient delivery of fluid, it is desirable to design pipes to reduce the Reynolds number. The Reynolds number Re is given by the following equation.

$$Re = (\rho v d)/\mu \qquad (4)$$

Here, $\rho$ is the density of the fluid, v is the average flow velocity of the pipe cross section, d is the pipe diameter, and $\mu$ is the viscosity of the fluid.

When applying fluid mechanics to the umbilical circulatory system, the umbilical cord artery can be considered a diversion duct and the umbilical cord vein can be considered a collecting duct. In the blood flow flowing through the umbilical cord vein that serves as a collecting duct, friction loss, contraction loss, and bending loss occur. These are determined by the merging velocity, the flow rate ratio, and the cross-sectional area ratio, all of which have little change. In addition, a vortex is generated at the confluence portion, replenishing the energy at the central portion and allowing the blood to move forward.

On the other hand, in the blood flow flowing through the umbilical cord artery that serves as the diversion duct, friction loss, bending loss, and expansion loss occur. Here, since the bending loss and the expansion loss are relatively small, the friction loss greatly contributes to the decrease in the flow velocity. In order to keep the boundary layer of the blood vessel wall thin so as not to cause an increase in the blood pressure due to the decrease of the flow velocity, the vascular endothelial cells that constitute the blood vessel wall tend to become rounded. As the vascular endothelial cells become rounded, the blood flow in the blood vessel walls swirls and is disturbed, replenishing the energy in the central portion and allowing the blood to move forward.

According to a study by German pathologist R. Toma et al., it was found that when blood flows through a blood vessel, shear stress is generated between the blood flow in the blood vessel and the vascular endothelial cells, by which the growth (thick blood vessels become thicker and thin blood vessels branch off) and regression (reduction or disappearance of blood vessels) of blood vessels is controlled.

Since such vascular growth and regression are applied from capillaries to large blood vessels, they also occur in the umbilical cord artery.

In addition, prostacyclin ($PGI_2$) and endothelium-derived relaxing factor (EDRF) are produced from vascular endothelial cells, and these act on vascular smooth muscles to expand blood vessels. On the other hand, endothelin, which is a peptide that strongly and continuously constricts blood vessels, is produced from vascular endothelial cells, and both of these act antagonistically and are balanced under normal conditions. In addition, like the relationship between $PGI_2$ and thromboxane, endothelial cells prevent the formation of blood clots, promote platelet aggregation, and produce substances associated with thrombolytic activity such as tissue plasminogen activators. The fetus develops when these are well balanced.

From the above findings, it can be said that if the shear stress between the blood flow in the umbilical cord artery and the vascular endothelial cells can be measured, the growth state of the fetus can be diagnosed. However, it is difficult to visualize or quantify the shear stress in blood vessels. Accordingly, the present inventor has found that the Reynolds number of the blood flow can be used as an indicator instead of shear stress. As discussed above, the Reynolds number can be a criterion for determining whether the blood flow is laminar flow or turbulent flow. It is presumed that the higher the degree of turbulence of the blood flow, the higher the shear stress between the blood flow and the vascular endothelial cells. If the shear stress is high, the vascular endothelial cells are stimulated and grow, and the fetus develops well.

The present inventor has repeated studies based on the above hypothesis, and has found a relationship between the Reynolds number of blood flow and the FGR of the fetus. The following is the content of the research actually performed by the present inventor.

Content of Research

The blood flow was measured using TOSHIBA SSA340A (Convex type PVF375DT3OOC) with an angle correction of 60 degrees or less. 42 pregnant women with natural pregnancies excluding fetal malformations and premature water breaking were arbitrarily extracted from outpatient and inpatient pregnant women as measurement subjects, and after obtaining consent, the patients were placed in a supine resting position and ultrasonic measurements were performed to simultaneously measure fetal body weight (Osaka University method) and Amniotic fluid index (AFI).

The Reynolds number Re of the fetal blood flow was calculated by substituting the average blood flow velocity (v), the diameter (d) of the arterial blood vessel, the blood density ($\rho$), and the blood viscosity ($\mu$) of the umbilical cord artery obtained by the ultrasonic measurement into the above equation (4). For both blood density ($\rho$) and blood viscosity ($\mu$), the average value of fetal blood was used.

Furthermore, in parallel with the above, fetuses with an estimated fetal weight of less than −1.5SD were diagnosed as FGR, and if not, it was regarded as a normal pregnancy. In addition, treatment (the administration of uterine contractile inhibitors) was given to pregnant women whose fetuses were diagnosed with FGR, and the results were used to distinguish between treatments having a treatment effect and those having no treatment effect.

Figure 2:
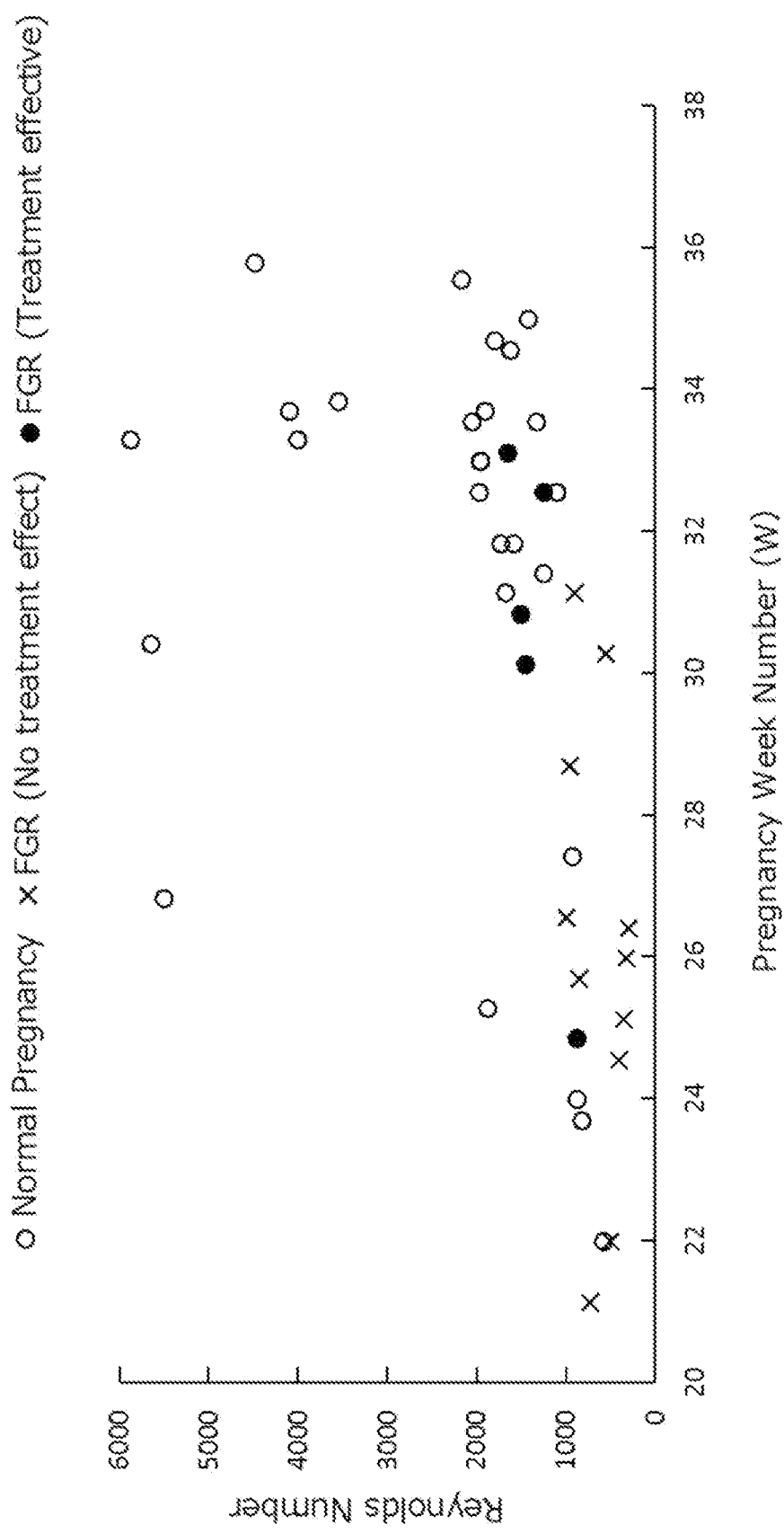
FIG. 2 is a graph illustrating the number of pregnancy weeks on the horizontal axis and, on the vertical axis, the Reynolds number obtained as a result of performing ultrasonic measurement using the inspection device of the present embodiments after having the pregnant woman take a supine resting position.

As a result of the above research, FIG. 2 illustrates a graph in which the presence or absence of FGR and the presence or absence of a treatment effect are plotted together with the Reynolds number. First, the present inventor found that the relationship between the Reynolds number and FGR is not clear when the pregnancy is less than 20 weeks. It is presumed that this is because the fetus is underdeveloped and the umbilical cord artery has not been sufficiently constructed when the pregnancy is less than 20 weeks.

On the other hand, the present inventor has found that after 20 weeks of pregnancy, the umbilical cord artery has been sufficiently constructed and the blood flow has stabilized, such that the Reynolds number can be appropriately measured. As a result, as illustrated in FIG. 2, the relationship between the Reynolds number and FGR becomes clear. According to the results illustrated in FIG. 2, after 20 weeks of pregnancy, division into a group including only normal pregnancies and a group including normal pregnancies and FGR is possible using a predetermined Reynolds number as a boundary. More particularly, if the Reynolds number is greater than or equal to 1800 (a first threshold value), it can be determined that the pregnancy is normal. On the other hand, if the Reynolds number is less than 1800, it can be determined that the fetus may have FGR, and a detailed examination and follow-up can be performed.

If the Reynolds number is greater than or equal to 1800, it is presumed that a considerable amount of turbulent flow components are also present in the blood flow flowing in the umbilical cord artery, thereby stimulating the vascular endothelial cells such that it can be presumed that the fetal growth is satisfactory. It should be noted that, even if the Reynolds number is less than 1800, although there are cases where the fetus is diagnosed as not currently having FGR, since there is a risk of developing FGR in the future, it is possible to give advice to improve the life of pregnant women.

Furthermore, according to the research results of FIG. 2, division into a group that may be cured from FGR by treatment and a group for which curing FGR by treatment is difficult can be performed with a predetermined Reynolds number as a boundary. More particularly, even if the Reynolds number is less than 1800, if it is greater than or equal to 800 (a second threshold), it can be determined that even if the fetus develops FGR, there is a possibility of curing the FGR by treatment. If the Reynolds number is greater than or equal to 800, although the turbulent flow components of the blood flow in the umbilical cord artery are small, since the vascular endothelial cells continue to be stimulated by the shear stress generated by the turbulent flow, it is presumed that a treatment effect can be expected. In particular, if the Reynolds number is greater than or equal to 1200, even if the fetus is diagnosed with FGR, subsequent treatment suggests that FGR is likely to be cured, thereby relieving the anxiety of the pregnant woman.

On the other hand, if the Reynolds number is less than 800, it can be determined that almost all the fetuses have FGR. In this case, stimulation of the vascular endothelial cells by the turbulent flow components of the blood flow in the umbilical cord artery is insufficient, and the treatment effect on FGR is presumed to be low. It should be noted that the first threshold value and the second threshold value are not limited to the above numerical values, and can be changed according to the conditions.

As described above, when the pregnancy week number is greater than or equal to 20 weeks, FGR can be tested using the Reynolds number, and therefore, even if a discrepancy in the pregnancy week number were to occur, there is little risk of the results of the test being affected.

On the other hand, the threshold value of the Reynolds number can be changed according to the pregnancy week number. For example, with reference to FIG. 2, the first threshold value may be set to 1200 for greater than or equal to 20 weeks of pregnancy and less than 30 weeks, and set to 1800 for greater than or equal to 30 weeks of pregnancy. In addition, the second threshold may be set to 800 for greater than or equal to 20 weeks of pregnancy and less than 30 weeks, and set to 1200 for greater than or equal to 30 weeks of pregnancy. In this manner, by changing the threshold value of the Reynolds number according to the pregnancy week number, it becomes possible to test for FGR with high accuracy. Hereinafter, a specific example of the FGR determination operation according to the pregnancy week number, which is executed by the inspection apparatus of FIG. 1, will be described.

Figure 3:
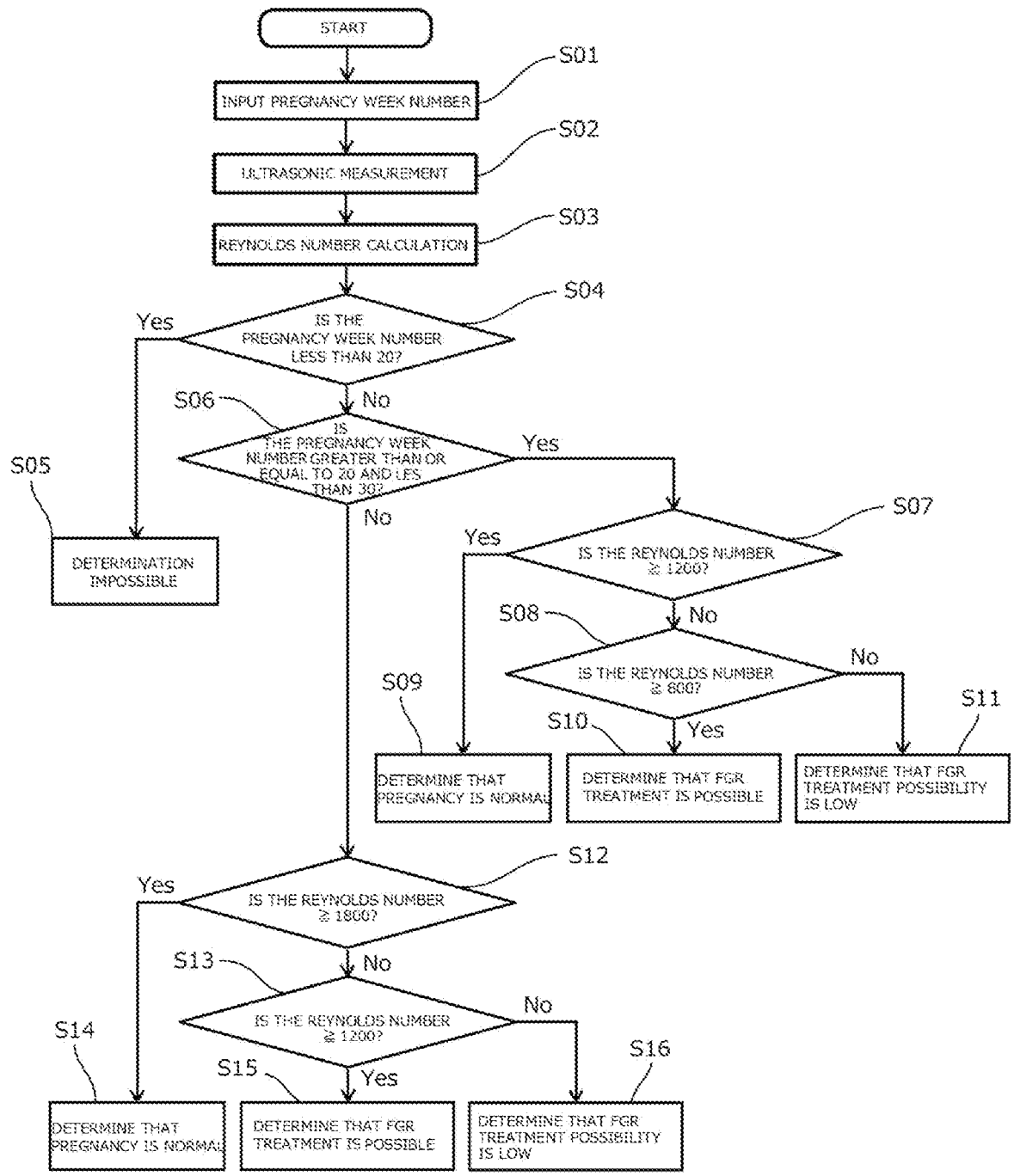
FIG. 3 is a flowchart illustrating a control operation of the inspection apparatus.

FIG. 3 is a flowchart illustrating a control operation of the inspection apparatus. It should be noted that it is assumed that the determination unit of the apparatus main body DB stores the first threshold value and the second threshold value corresponding to the pregnancy week number in an internal memory in advance.

In Step S01 of FIG. 3, when the pregnancy week number is input using a keyboard or the like when examining the growth state of the fetus, in Step S02, the apparatus main body DB receives a signal from the ultrasonic probe SWP applied to the pregnant woman, and in the subsequent Step S03, the calculation unit calculates the Reynolds number. Further, in Step S04, the determination unit determines whether or not the input pregnancy week number is less than 20 weeks. When it is determined that the input pregnancy week number is less than 20 weeks, the determination unit determines that determination of FGR is impossible in Step S05, and displays that determination is impossible on the monitor MN, for example.

On the other hand, when it is determined that the input pregnancy week number is not less than 20 weeks, the determination unit determines whether or not the input pregnancy week number is greater than or equal to 20 weeks and less than 30 weeks in the subsequent Step S06. When it is determined that the input pregnancy week number is greater than or equal to 20 weeks and less than 30 weeks, in Step S07, the determination unit determines whether or not the calculated Reynolds number is greater than or equal to 1200 (the first threshold).

When it is determined that the calculated Reynolds number is greater than or equal to 1200, the determination unit determines in Step S09 that the tested pregnant woman has a normal pregnancy (the fetus has not developed FGR). On the other hand, when it is determined that the calculated Reynolds number is less than 1200, the determination unit determines whether or not the calculated Reynolds number is greater than or equal to 800 (the second threshold value) in Step S08.

When it is determined that the calculated Reynolds number is greater than or equal to 800, the determination unit determines in Step S10 that the tested fetus may have FGR, and determines that there is a treatment possibility if FGR is present. On the other hand, when it is determined that the calculated Reynolds number is less than 800, the determination unit determines in Step S11 that the tested fetus may have FGR, and determines that the possibility of treatment is low if FGR is present.

On the other hand, when it is determined in Step S06 that the input pregnancy week number is greater than or equal to 30 weeks, in Step S12, the determination unit determines whether or not the calculated Reynolds number is greater than or equal to 1800 (first threshold).

When it is determined that the calculated Reynolds number is greater than or equal to 1800, the determination unit determines in Step S14 that the tested pregnant woman has a normal pregnancy (the fetus has not developed FGR). On the other hand, when it is determined that the calculated Reynolds number is less than 1800, the determination unit determines whether or not the calculated Reynolds number is greater than or equal to 1200 (the second threshold value) in Step S13.

When it is determined that the calculated Reynolds number is greater than or equal to 1200, the determination unit determines in Step S15 that the tested fetus may have FGR, and determines that there is a treatment possibility if FGR is present. On the other hand, when it is determined that the calculated Reynolds number is less than 1200, the determination unit determines in Step S16 that the tested fetus may have FGR, and determines that the possibility of treatment is low if FGR is present. The determination results described above are transmitted from the apparatus main body DB to the monitor MN, and the information is displayed.

According to the inspection apparatus of the present embodiments, the presence or absence of a possibility of FGR can be immediately determined by simply calculating the Reynolds number of the blood flow in the umbilical cord artery using ultrasounds that are non-invasive to the mother and the fetus. Accordingly, by simply performing ultrasonic measurements at the time of regular medical examinations for pregnant women, effective screening for the presence or absence of FGR that is easier than obtaining the estimated fetal weight according to the EFW method and more accurate than measuring the uterine cavity length becomes possible. Further, when it is determined that FGR may be present, further detailed testing can be performed individually. As a result, if a definitive diagnosis of FGR is made, it is possible to increase the number of cases of transition to normal pregnancy by providing early treatment and guidance for improving the life of pregnant women.

The present invention is not limited to the above embodiments. For example, if there are other means by which the inner diameter of the umbilical cord artery and the blood flow velocity can be detected, they may optionally be used to calculate the Reynolds number.

(FGR Diagnostic Method Using Reynolds Number)

An FGR diagnostic method includes measuring an inner diameter and a blood flow velocity of an artery extending from a fetus to a placenta of a pregnant woman; calculating a Reynolds number based on the inner diameter and the blood flow velocity of the artery measured by the measurement apparatus; and determining, based on a pregnancy week number and the Reynolds number, whether or not the fetus is developing FGR.

The FGR diagnostic method includes determining that the fetus may be developing FGR in a case that the Reynolds number is less than a first threshold value at a predetermined pregnancy week number.

The FGR diagnostic method includes determining that the fetus has not developed FGR in a case that the Reynolds number is greater than or equal to a first threshold value at a predetermined pregnancy week number.

The FGR diagnostic method includes modifying the first threshold value according to the pregnancy week number.

The FGR diagnostic method includes determining, in a case that the Reynolds number is less than the first threshold value but greater than or equal to a second threshold value at a predetermined pregnancy week number, that even if the fetus develops FGR, treatment may cure the FGR.

The FGR diagnostic method includes modifying the second threshold according to the pregnancy week number.

REFERENCE SIGNS LIST

AR ... Aorta, AV ... Ductus venosal, DB ... Apparatus main body, EH ... Foramen ovale, HT ... Fetal heart, LA ... Left atrium, LR ... Left ventricle, MN ... Monitor, PL ... Placenta, RA ... Right atrium, RR ... Right ventricle, SW ... Ultrasonic, SWP ... Ultrasonic probe, UCA ... Umbilical cord artery, UCV ... Umbilical cord vein, UV ... Inferior vena cava

The invention claimed is:

1. An inspection apparatus comprising:
a measurement apparatus that measures an inner diameter and a blood flow velocity of an artery extending from a fetus to a placenta of a pregnant woman;
a calculation apparatus that calculates a Reynolds number based on the inner diameter and the blood flow velocity of the artery measured by the measurement apparatus;
an input apparatus that inputs a pregnancy week number of the pregnant woman;
a determination apparatus that determines, based on the pregnancy week number and the Reynolds number, whether or not the fetus is developing a fetal growth restriction, which is termed as FGR;
the determination apparatus determines that the fetus may be developing FGR in a case that the Reynolds number is less than a first threshold value at the inputted pregnancy week number; and
the first threshold value is set to 1200 for greater than or equal to 20 weeks of pregnancy and less than 30 weeks, and set to 1800 for greater than or equal to 30 weeks of pregnancy.

2. The inspection apparatus according to claim 1, wherein the determination apparatus determines that the fetus has not developed FGR in a case that the Reynolds number is greater than or equal to the first threshold value at the inputted pregnancy week number.

3. The inspection apparatus according to claim 1, wherein the determination apparatus modifies the first threshold value according to the inputted pregnancy week number.

4. The inspection apparatus according to claim 1, wherein the determination apparatus determines, in a case that the Reynolds number is less than the first threshold value but greater than or equal to a second threshold value at the inputted pregnancy week number, that even if the fetus develops FGR, treatment may cure the FGR.

5. The inspection apparatus according to claim 4, wherein the determination apparatus modifies the second threshold according to the inputted pregnancy week number.

6. The inspection apparatus according to claim 4, wherein the first threshold value is set to 1200 for greater than or equal to 20 weeks of pregnancy and less than 30 weeks, and set to 1800 for greater than or equal to 30 weeks of pregnancy, and the second threshold is set to 800 for greater than or equal to 20 weeks of pregnancy and less than 30 weeks, and set to 1200 for greater than or equal to 30 weeks of pregnancy.

7. The inspection apparatus according to claim 1, wherein the measurement apparatus includes an ultrasonic probe for irradiating an ultrasonic wave to the artery, and detects the inner diameter and the blood flow velocity of the artery based on a reflected wave of the ultrasonic wave.

8. An inspection apparatus comprising:
a measurement apparatus that measures an inner diameter and a blood flow velocity of an artery extending from a fetus to a placenta of a pregnant woman;
a calculation apparatus that calculates a Reynolds number based on the inner diameter and the blood flow velocity of the artery measured by the measurement apparatus;
an input apparatus that inputs a pregnancy week number of the pregnant woman;
a determination apparatus that determines, based on the pregnancy week number and the Reynolds number, whether or not the fetus is developing a fetal growth restriction, which is termed as FGR;
the determination apparatus determines that the fetus may be developing FGR in a case that the Reynolds number is less than a first threshold value at the inputted pregnancy week number;
the determination apparatus determines that the fetus has not developed FGR in a case that the Reynolds number is greater than or equal to the first threshold value at the inputted pregnancy week number; and
the first threshold value is set to 1200 for greater than or equal to 20 weeks of pregnancy and less than 30 weeks, and set to 1800 for greater than or equal to 30 weeks of pregnancy.

9. The inspection apparatus according to claim 8, wherein the measurement apparatus includes an ultrasonic probe for irradiating an ultrasonic wave to the artery, and detects the inner diameter and the blood flow velocity of the artery based on a reflected wave of the ultrasonic wave.

10. An inspection apparatus comprising:
a measurement apparatus that measures an inner diameter and a blood flow velocity of an artery extending from a fetus to a placenta of a pregnant woman;
a calculation apparatus that calculates a Reynolds number based on the inner diameter and the blood flow velocity of the artery measured by the measurement apparatus;
an input apparatus that inputs a pregnancy week number of the pregnant woman;
a determination apparatus that determines, based on the pregnancy week number and the Reynolds number, whether or not the fetus is developing a fetal growth restriction, which is termed as FGR;
the determination apparatus determines that the fetus may be developing FGR in a case that the Reynolds number is less than a first threshold value at the inputted pregnancy week number; and
the determination apparatus determines, in a case that the Reynolds number is less than the first threshold value but greater than or equal to a second threshold value at the inputted pregnancy week number, that even if the fetus develops FGR, treatment may cure the FGR.

11. The inspection apparatus according to claim 10, wherein the determination apparatus modifies the second threshold according to the inputted pregnancy week number.

12. The inspection apparatus according to claim 10, wherein the first threshold value is set to 1200 for greater than or equal to 20 weeks of pregnancy and less than 30 weeks, and set to 1800 for greater than or equal to 30 weeks of pregnancy, and the second threshold is set to 800 for greater than or equal to 20 weeks of pregnancy and less than 30 weeks, and set to 1200 for greater than or equal to 30 weeks of pregnancy.

13. The inspection apparatus according to claim 10, wherein the measurement apparatus includes an ultrasonic probe for irradiating an ultrasonic wave to the artery, and detects the inner diameter and the blood flow velocity of the artery based on a reflected wave of the ultrasonic wave.

\* \* \* \* \*